United States Patent
Mansour (10) Patent No.: US 9,724,464 B2
(45) Date of Patent: Aug. 8, 2017

(54) PASSIVE RESTART Y-SITE

(71) Applicant: CareFusion 303, Inc., San Diego, CA (US)

(72) Inventor: George Mansour, Ontario, CA (US)

(73) Assignee: CareFusion 303, Inc., San Diego, CA (US)

(*) Notice: Subject to any disclaimer, the term of this patent is extended or adjusted under 35 U.S.C. 154(b) by 341 days.

(21) Appl. No.: 14/319,948

(22) Filed: Jun. 30, 2014

(65) Prior Publication Data

US 2015/0374910 A1    Dec. 31, 2015

(51) Int. Cl.
  *A61M 5/168*    (2006.01)
  *A61M 5/14*    (2006.01)
  (Continued)

(52) U.S. Cl.
  CPC ........ *A61M 5/16827* (2013.01); *A61M 1/005* (2014.02); *A61M 5/1408* (2013.01); *A61M 5/1409* (2013.01); *A61M 5/1413* (2013.01); *A61M 5/16804* (2013.01); *A61M 5/40* (2013.01); *A61M 39/24* (2013.01); *A61M 2039/2433* (2013.01)

(58) Field of Classification Search
  CPC  A61M 5/1411; A61M 5/168; A61M 5/16804; A61M 5/16813; A61M 5/1684; A61M 5/1685; A61M 5/16877; A61M 5/40; A61M 5/16881; A61M 1/005; A61M 5/16827
  USPC ......................................... 604/246, 251, 254
  See application file for complete search history.

(56) References Cited

U.S. PATENT DOCUMENTS 2,784,733 A * 3/1957 Martinez ................. A61M 5/40
                                                    137/399
4,256,103 A * 3/1981 Mylrea ............... A61M 5/1408
                                                    137/113
(Continued)

FOREIGN PATENT DOCUMENTS

| CN | 102727957 A | 10/2012 |
|---|---|---|
| CN | 102743809 A | 10/2012 |
| CN | 102973997 A | 3/2013 |

OTHER PUBLICATIONS

International Search Report and Written Opinion for Application No. PCT/US2015/036288, dated Sep. 17, 2015, 10 pages.
(Continued)

*Primary Examiner* — Nathan R Price
*Assistant Examiner* — Melissa A Snyder
(74) *Attorney, Agent, or Firm* — McDermott Will & Emery LLP (57) ABSTRACT

A fluid delivery Y-site is described that is configured to receive and control delivery of two or more fluid flows. Fluid flow is controlled within a chamber by a valve and float. Flow of a primary fluid into the chamber is reduced or halted by the movement of a valve. The valve may occlude a first flow port into the chamber in response fluid flowing from a second flow port into the chamber. A float is moveably disposed within the chamber and configured to engage the valve in response a fluid flow into the chamber from the second flow port. As fluid flow from the second flow port into the chamber is reduced or ceases, the valve and float allow the flow from the primary flow port to once again enter the chamber and exit from an outlet port.

19 Claims, 5 Drawing Sheets

(51) Int. Cl.
*A61M 39/24* (2006.01)
*A61M 5/40* (2006.01)
*A61M 1/00* (2006.01)

(56) References Cited

U.S. PATENT DOCUMENTS

| | | |
|---|---|---|
| 4,449,976 A | 5/1984 | Kamen |
| 5,839,466 A * | 11/1998 | Dutter ............... A01K 7/04 |
| | | 119/78 |
| 6,213,986 B1 | 4/2001 | Darling, Jr. |
| 6,485,454 B1 | 11/2002 | Yueh |
| 2007/0215637 A1 | 9/2007 | Kim |
| 2009/0287152 A1* | 11/2009 | Goodall ............ A61M 5/1411 |
| | | 604/127 |
| 2010/0024114 A1* | 2/2010 | Hand .................... E03D 1/34 |
| | | 4/395 |
| 2011/0275988 A1 | 11/2011 | Davis et al. |
| 2013/0331811 A1 | 12/2013 | Butterfield |

OTHER PUBLICATIONS

International Search Report and Written Opinion for Application No. PCT/US2015/036289, dated Oct. 2, 2015, 10 pages.

\* cited by examiner

PASSIVE RESTART Y-SITE

BACKGROUND

This invention relates in general to the field of medical fluid connectors, and in particular to a Y-site connector for use in medical infusion therapy.

Medical infusion therapy involves the administration of medication through a needle or catheter. The medication may be administered using intravenous, intramuscular, or epidural techniques. Typically, infusion therapy includes a fluid source coupled to a patient's intravenous needle or a catheter through tubing. The fluid source, which may comprise medication, a diluent, or any other fluid, is usually dripped from the fluid source, through the tubing, and into the patient. To facilitate the introduction of an additional fluid into the patient, a Y-site device or connector ("Y-site") may be installed in the fluid pathway between a fluid source and the patient.

The Y-site provides a port where a secondary fluid source may be coupled to the fluid pathway established between a primary fluid source and the patient. To control the flow of fluid from the primary and secondary fluid source, each fluid source is suspended at a specific height. For example, a secondary fluid source containing medication may be joined to the fluid pathway having a primary fluid source containing a diluent such that the medication is delivered to the patient during fluid flow from the primary fluid source to the patient.

SUMMARY

An aspect of the present disclosure provides a fluid delivery Y-site device comprising: a chamber fluidly coupled between a primary flow port and an exit flow port; one or more a secondary flow port fluidly coupled to the chamber, the secondary flow port configured to conduct fluid to the chamber; and a valve positioned adjacent the primary flow port, the valve configured to move between an occluding configuration and an open configuration, based on a level of fluid within the chamber, such that the valve controls fluid flow through the primary flow port and into the chamber.

According to certain implementations of the present disclosure, A method of controlling fluid through a Y-site device, comprising: providing a chamber fluidly coupled between a primary flow port and an exit flow port; providing a secondary flow port fluidly coupled to the chamber, the secondary flow port configured to conduct fluid to the chamber; providing a valve positioned adjacent the primary flow port; and moving, based on a level of fluid within the chamber, the valve between an occluding configuration and an open configuration, such that the valve controls fluid flow through the primary flow port and into the chamber.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such as "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Figure 1:
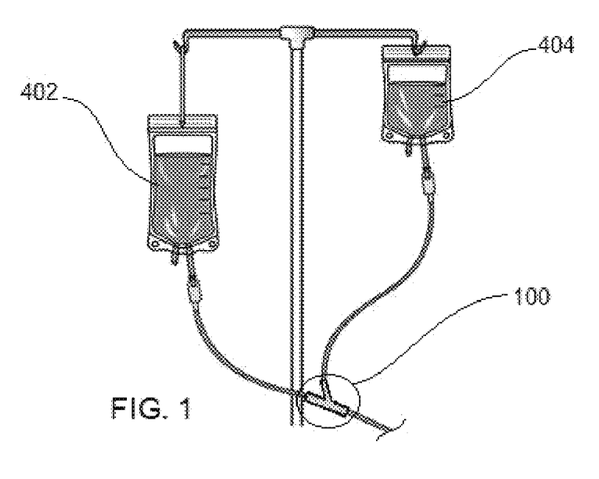
FIG. 1 illustrates a Y-site used in medical infusion therapy.

The present disclosure relates to a passive restart Y-site for use in medical infusion therapy. FIG. 1 illustrates a passive restart Y-site 100 fluidly coupled to a primary fluid source 402 and a secondary fluid source 404. The passive restart Y-site 100 is configured to receive and control delivery of the primary fluid 402 and the secondary fluid 404 to a patient (not shown). In some instances, the fluid is directed through an infusion pump (also not shown) prior to being directed to the patient.

Figures 2A, 2B:
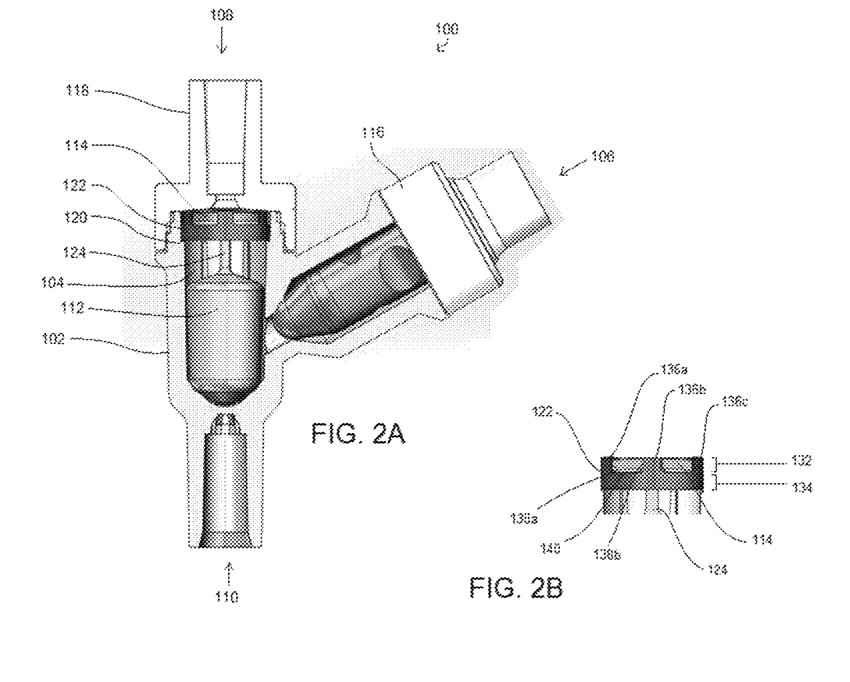
FIG. 2A illustrates a front view of an embodiment of a passive restart Y-site in an open configuration in accordance with aspects of the present disclosure.
FIG. 2B illustrates a sectional view of portion of the passive restart Y-site of FIG. 2A.
Figure 3:
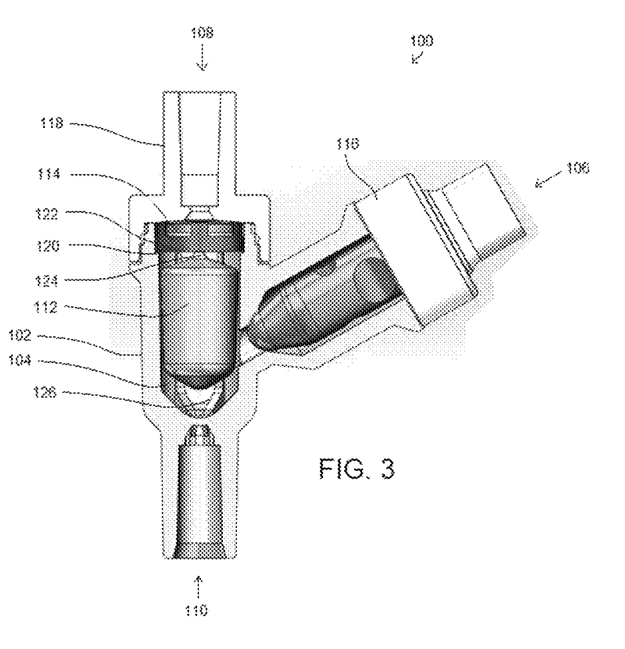
FIG. 3 illustrates a front view of an embodiment of a passive restart Y-site in a first configuration in accordance with aspects of the present disclosure.

Referring to FIGS. 2A-3, the passive restart Y-site 100 comprises a body 102 forming a chamber 104, two or more flow ports where fluid may enter the chamber 104, and a port where fluid may exit the chamber 104. In some embodiments, the body 102 comprises a port where a primary fluid 402 may enter the body 102, a port where a secondary fluid 404 may enter the body 102, and a port for either fluid to exit the body 102. In a preferred embodiment, the body 102 comprises a top port 108 and a bottom port 110 with the chamber 104 therebetween. A side port 106 is fluidly connected to the chamber 104 between the top port 108 and bottom port 110. A primary fluid 402 may enter the chamber 104 from the top port 108, while a secondary fluid 404 may enter the chamber 104 from the side port 106. Fluid that enters the chamber 104 from either port may exit the chamber from the bottom port 110. A fluid source may be coupled with the top port 108 or side port 106 using a fluid fitting such as a luer-type fitting. In a preferred embodiment, the side port 106 comprises a needleless access valve 116.

Flow of two or more fluids to a patient is passively controlled within the body 102. More specifically, flow of a primary fluid 402 from the top port 108 into the chamber 104 is reduced or halted upon the fluid within the chamber 104 exceeding a filling threshold. The filling threshold may be exceeded as a result of a primary fluid 402 entering the chamber 104 from the top port 108 or a secondary fluid 404 entering the chamber 104 from the side port 106. When the fluid within the chamber 104 fills to exceed the filling threshold, the flow of the primary fluid 402 from the top port 108 into the chamber 104 is reduced or halted by movement of a valve 114 and float 112. When the fluid level within the chamber 104 drains through the exit or bottom port 110, the fluid level within the chamber 104 will decrease. When the fluid level is below the filling threshold, for example, when the secondary fluid flow 404 from the side port 106 into the chamber 104 is reduced or ceases, the valve 114 and float 112 follow the fluid level and move to allow the primary fluid 402 to once again flow into the chamber 104.

The Y-site operates to prioritize communication of the fluid to the patient. In some embodiments, the Y-site is designed to communicate the second fluid through the chamber before communicating the entire reservoir of the first fluid. It prioritizes what is communicated through the chamber by halting flow of the primary fluid until the secondary fluid has been communicated through the chamber. By halting flow of the primary fluid 402 upon introduction of the secondary fluid 404, complete delivery of the secondary fluid 404 to the patient may be assured before flow of the primary fluid 402 is resumed. When flow of the primary fluid 402 is partially halted, combined secondary fluid 404 and primary fluid 402 may be delivered to the patient in a specific ratio.

The body 102 may be any shape, including a cylinder or elongate having a cross-section that is a sphere, square, or rectangle. In a preferred embodiment, the body is cylindrically shaped. The body 102 may be composed of any rigid material such as a polycarbonate, acrylonitrile butadiene styrene (ABS), or polystyrene. The body 102 and chamber 104 may be a size that achieves the desired flow rate and volume. For example, the chamber 104 volume may be selected to achieve a specific flow rate or to retain specific float 112 or valve 114 sizes. The body 102 may further comprise a bleed off valve or filter (not shown), such as a hydrophobic filter, to allow air to escape from within the chamber 104. In some embodiments, the body 102 comprises a lens or other visual indicator (not shown) of flow movement or float position within the body 102.

In a preferred embodiment the body 102 has a top port 108, a bottom port 110 opposite the top port 108, and a side port 106 disposed between the top port 108 and bottom port 110. However, the ports may be oriented in any location on the body 102. For example, the top port 108 and side port 106 may be disposed at the top of the body 102 with each port having a respective flow path through the body 102 and into the chamber 104. In some embodiments, any of the ports may be formed as a cap 118 coupled to the body 102. In a preferred embodiment, the cap 118 is removably coupled to the body, thereby providing access to the chamber 104. In some embodiments, the cap 118 is adjustable to reduce or enlarge the chamber 104 volume, alter fluid flow through the chamber 104, or vary the buoyancy of the float 112.

Figure 4:
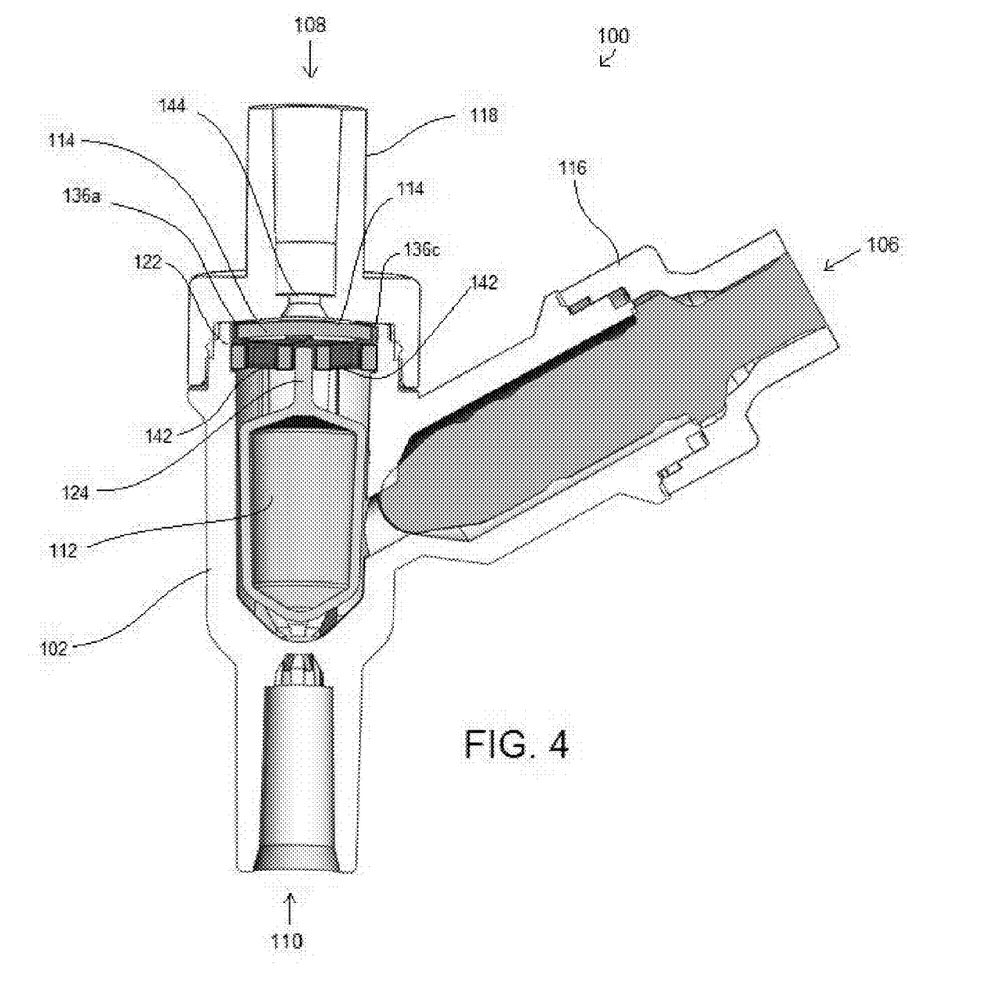
FIG. 4 illustrates a sectional view of an embodiment of a passive restart Y-site in a second configuration in accordance with aspects of the present disclosure.

Referring to FIG. 2B, a valve guide 122 may be disposed in the chamber 104 proximate the top port 108. The valve guide 122 comprises and upper portion 132 and a lower portion 134. The perimeter of the upper portion 132 comprises a plurality of fingers (e.g., 136a, 136b, 136c) that extend from the lower portion 134. Adjacent fingers, for example 136a and 136b, have opposing edges 138a and 138b separated apart by a distance. A lower edge 140 is formed between the opposing edges 138a and 138b by a top edge of the lower portion 134. Opposing edges 138a and 138b, and lower edge 140 create a peripheral opening through the perimeter of the upper portion 132. Referring to the embodiment illustrated in FIG. 4, the lower potion 134 comprises one or more longitudinally oriented apertures 142 disposed through the cross-section of the valve guide 122. In some embodiments, the apertures 142 are offset from the central axis of the valve guide 122.

A valve 114 may be disposed in the chamber 104 proximate the top port 108 such that the valve 114 is positioned between the fingers 136a, 136b, 136c of the upper portion 132. The valve 114 may be cylindrically shaped with a convex and concaved surface, and wherein a circumferential edge of the concaved surface is engaged or is configured to engage with a lower portion 134 of the valve guide 122. In an open configuration, a fluid flow from the top port 108 may enter the chamber 104 from an aperture 144 through the cap 118. The fluid may then pass over the convex surface and around the circumferential edge of the valve 114. The peripheral openings through the perimeter of the upper portion 132 allows the fluid to flow beneath the concave surface of the valve 114 and through the apertures 142 of the lower portion 134.

The valve 114 is configured to occlude the aperture 144 of the top port 108 upon fluid within the chamber 104 exceeding a filling threshold. In some embodiments, the valve 114 only partially occludes the top port 108 upon exceeding a filling threshold, allowing flow from both the top port 108 and side port 106 into the chamber 104. Preferably, the shape of the valve 114 is a large disk having a broad surface, wherein the valve 114 is activated by fluid pressure from a secondary fluid 404 flow upon the broad surface. In some embodiments, the valve 114 is shaped as a cone, sphere, or any other shape that may be activated by fluid to occlude the top port 108. In some embodiments, the valve 114 is elastically deformed when activated by the presence of fluid pressure within the chamber 104.

The valve 114 may be fabricated from a malleable rubber, silicone, plastic, or thermoplastic elastomer. The valve 114 dimensions may be selected to achieve activation or movement of the valve 114 upon a specific fluid pressure. For example, a valve 114 thickness may be selected to partially or fully occlude the top port 108 in response to a specified fluid level or fluid pressure. In some embodiments, the valve 114 partially occludes the top port 108 at a first fluid pressure, and then fully occludes the top port 108 at a second fluid pressure. A valve seat 120, configured to retain the valve 114, may be disposed in the body 102 proximate the top port 108. A first side of the valve seat 120 may be formed as a circumferential ridge in the chamber 104 while the second side may be formed by the top port 108. In some embodiments, the second side of the valve seat may be an arcuate surface. A valve guide 122 may also be disposed in the chamber 104 proximal to the top port 108. In some embodiments, the valve seat 102 is configured to retain the valve guide 122 and valve 114. The valve guide 122 may be shaped as a basket to retain and guide the valve 114 in the chamber 104. The valve guide 122 may have one or more aperture through its cross-section to allow fluid flow through the valve guide 122. Preferably, the valve guide 122 is composed of a rigid material to protect against unintentional deformation of the valve 114.

The float 112 may be disposed in the chamber 104 between the valve 114 and bottom port 110. The float 112 comprises specific buoyancy and is configured to move within the chamber 104 between the top port 108 and bottom port 110 in response to fluid flow. The float 112 may include a protrusion 124 that extends partially toward the valve 114. When the float 112 rises, the protrusion 124 may engage the valve 114, assuring the valve 114 remains in the activated position. In some embodiments, the protrusion 124 and valve 114 are coupled, whereby the protrusion 124 and valve 114 move in unison within the chamber 104. An aperture through the valve guide 122 allows the protrusion 124 to pass through the valve guide 122 unobstructed. In some embodiments, the float 112 comprises radial protrusions or grooves on an outer surface to allow fluid flow past the float 112 when the float is in contact with a port. For example, fluid may continue to exit the chamber 104 when the float is in a lowered position that would otherwise occlude the bottom port 110. In some embodiments the float 112 or chamber 104 comprises an annular ring 126 or seat such that the bottom port 110 becomes occluded when the float 112 is in a lowermost position, thereby preventing air from passing through the chamber 104 to the patient.

The float 112 may comprise specific buoyancy such that a specific fluid level within the chamber causes the float 112 to rise or lower in the chamber. The float may be solid or hollow, and may comprise air or foam. Preferably, the material used to fabricate the float 112 will not degrade in the particular environment. In some embodiments, all or a portion of the float 112 is coated with a non-degrading material. The buoyancy characteristics of the float 112 may be varied by rotation of a dial or selector. For example, the float 112 may be configured as two portions coupled together. The two portions of the float 112 may be rotated to increase or decrease the volume within the float 112. In some embodiments, the buoyancy of the float 112 is varied by altering the interior volume of the float 112. For example, the float 112 may be configured with an inner bladder fillable through a valve in a surface of the float 112.

During fluid flow from the top port 108 the valve 114 would remain in an open or deactivated position, and the float 112 would remain between the valve 114 and bottom port 110, thereby allowing fluid flow from the top port 108 to enter the chamber 104 and exit from the bottom port 110. Upon fluid within the chamber 104 exceeding a filling threshold, such as by introduction of a fluid flow from the side port 106 or from the top port 108, the fluid would cause the valve 114 to be activated and occlude the top port 108. Additionally, the float 112 may rise and engage the valve 114, assuring the valve 114 remains activated. In this occluded configuration, fluid that remains in the chamber 104, and fluid flow from the side port 106, would enter the chamber 104 and exit from the bottom port 110. Once the fluid drains from the bottom port 110, the float 112 will drop with the fluid level in the chamber 104, and reopen the top port 108, thereby again permitting flow through the top port 108 to enter the chamber 104. This is one example of how the Y-site passively stops and restarts based on the level of fluid within the chamber.

In some embodiments, the valve 114 and float 112 are configured to partially occlude the top port 108, allowing a combined fluid flow from the top port 108 and side port 106 to enter the chamber 104 and exit from the bottom port 110. Upon a reduction of fluid within the chamber 104 to below the filling threshold, or a reduction or completion of fluid flow from the side port 106, an open position would be achieved. In an open position, the float 112 would lower and the valve 114 would disengage or open, thereby allowing fluid flow from the top port 108 to enter the chamber 104 and exit from the bottom port 110.

Figure 5:
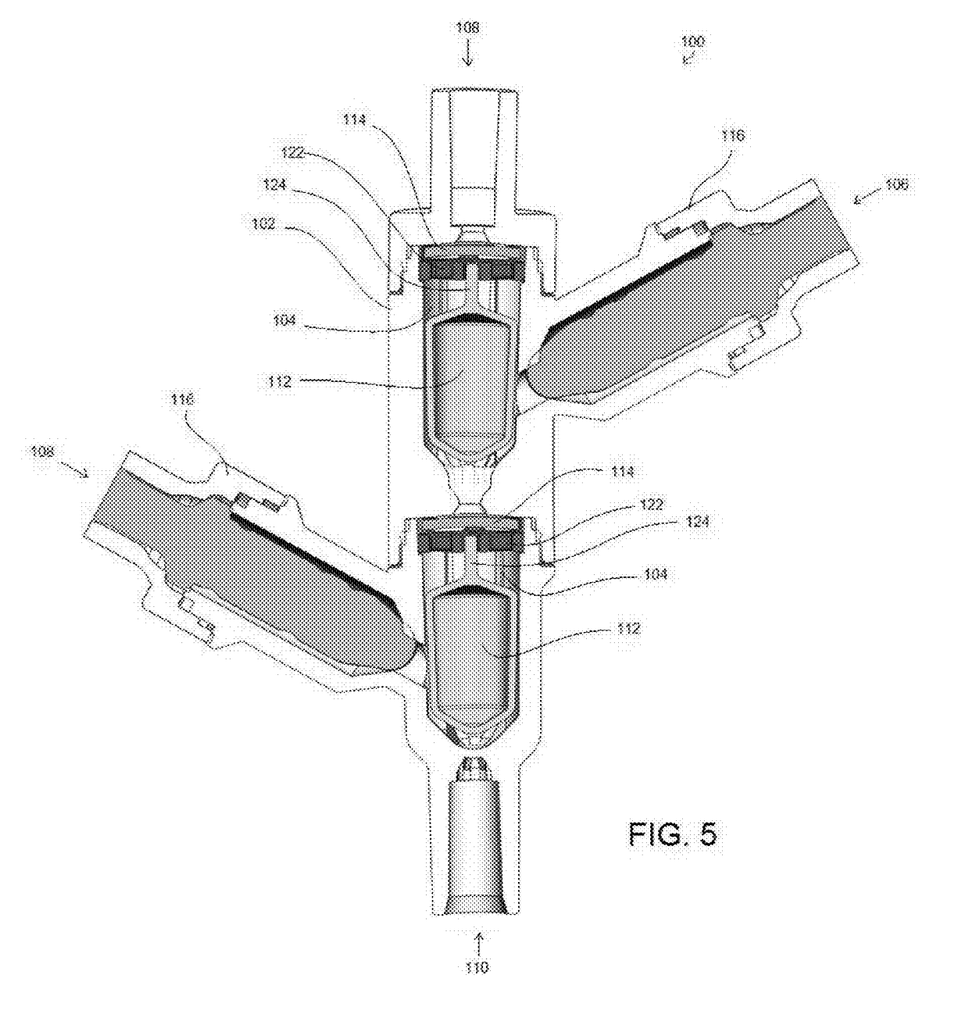
FIG. 5 illustrates a sectional view of an embodiment of a passive restart Y-site in a second configuration in accordance with aspects of the present disclosure.

In some embodiments, the float 112 comprises two or more protrusions 124 configured to engage a valve 114. In some embodiments the body 102 comprises two or more chambers 104 and floats 112, allowing for two or more primary fluids 402 or secondary fluids 404 to be coupled with the passive restart Y-site 100 as illustrated in FIG. 5. In some embodiments where multiple primary fluids 402 or secondary fluids 404 are coupled to the passive restart Y-site 100, a selector may be utilized to determine the sequence of primary or secondary flows into the chamber 104.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim. The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." The term "some" refers to one or more. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

Described herein are at least the following concepts:

Concept 1. A fluid delivery Y-site device comprising:
a chamber fluidly coupled between a primary flow port and an exit flow port;
a secondary flow port fluidly coupled to the chamber, the secondary flow port configured to conduct fluid to the chamber; and
a valve positioned adjacent the primary flow port, the valve configured to move between an occluding configuration and an open configuration, based on a level of fluid within the chamber, such that the valve controls fluid flow through the primary flow port and into the chamber.

Concept 2. The device of concept 1, further comprising a float disposed within the chamber between the valve and the exit flow port, the float configured to (i) move within the chamber and (ii) move the valve to the occluding configuration when the level of fluid within the chamber exceeds a filling threshold.

Concept 3. The device of concept 2, wherein the float is configured to permit transition of the valve to the open configuration when the level of fluid within the chamber is below the filling threshold.

Concept 4. The device of concept 2, wherein the float is configured to occlude the exit flow port when the level of fluid within the chamber is below a draining threshold.

Concept 5. The device of concept 4, further comprising an annular ring disposed proximal to the exit flow port, the float being configured to engage the annular ring, such that the engagement between the float and the ring restricts air from exiting the chamber through the exit flow port.

Concept 6. The device of concept 1, further comprising a valve seat formed in the chamber proximate the primary flow port.

Concept 7. The device of concept 1, further comprising a valve guide disposed in the chamber proximate the primary flow port, the valve disposed at least partially within the valve guide, and the valve guide configured to guide the valve between the occluding configuration and the open configuration.

Concept 8. The device of concept 1, wherein the valve is a disk having a convex surface that is configured to face the primary flow port and a concave surface that is configured to face away from the primary flow port, the disk being configured to be elastically deformed based on the level of fluid within the chamber.

Concept 9. The device of concept 1, wherein the secondary flow port comprises a needleless access valve.

Concept 10. The device of concept 1, wherein the secondary flow port is connected to the chamber at an angle relative of between about 20 degrees and about 60 degrees from a longitudinal axis of the chamber.

Concept 11. The device of concept 2, wherein the float comprises a protrusion extending from the float toward the valve, such that the protrusion engages the valve when the float moves the valve to the occluding configuration.

Concept 12. The device of concept 11, wherein the protrusion extends through the valve guide and engages the valve when the level of fluid within the chamber exceeds the filling threshold.

Concept 13. The device of concept 2, wherein the float comprises variable interior volume, such that buoyancy of the float can be adjusted.

Concept 14. The device of concept 2, further comprising an indicator that provides visual indication that the float has moved the valve to the occluding configuration.

Concept 15. The device of concept 14, wherein the indicator comprises a transparent window in a wall of the chamber, the transparent window forming a lens.

Concept 16. The device of concept 1, wherein the chamber comprises an air valve configured to release air from within the chamber.

Concept 17. A method of controlling fluid through a Y-site device, comprising:
providing a chamber fluidly coupled between a primary flow port and an exit flow port;
providing a secondary flow port fluidly coupled to the chamber, the secondary flow port configured to conduct fluid to the chamber;
providing a valve positioned adjacent the primary flow port; and
moving, based on a level of fluid within the chamber, the valve between an occluding configuration and an open configuration, such that the valve controls fluid flow through the primary flow port and into the chamber.

Concept 18. The method of concept 17, wherein the valve is moved by a float disposed within the chamber between the valve and the exit flow port, the float moving the valve to the occluding configuration when the level of fluid within the chamber exceeds a filling threshold.

Concept 19. The method of concept 18, further comprising engaging the valve with the float when moving the valve to the occluding configuration and disengaging the float and the valve when the level of fluid is below the filling threshold.

Concept 20. The method of concept 18, further comprising occluding the exit flow port when the level of fluid within the chamber is below a draining threshold.

What is claimed is:

1. A fluid delivery Y-site device comprising:
a chamber fluidly coupled between a primary flow port and an exit flow port;
a secondary flow port fluidly coupled to the chamber, the secondary flow port configured to conduct fluid to the chamber;
a valve guide, positioned in the chamber proximate the primary flow port;
a valve positioned between the primary flow port and the valve guide, the valve configured to move between an occluding configuration and an open configuration, based on a level of fluid within the chamber, wherein in the occluding configuration, the valve is engaged against the primary flow port to occlude a fluid flow through the primary flow port into the chamber, and in the open configuration, the valve is separated from the primary flow port to permit a fluid flow through the primary flow port into the chamber; and a float positioned within the chamber between the valve and the exit flow port, the float configured to move independent of the valve based on a level of fluid within the chamber, such that a portion of the float extends through the valve guide and engages the valve to move the valve to the occluding configuration.

2. The device of claim 1, wherein the valve is moved to the occluding configuration when the level of fluid within the chamber exceeds a filling threshold.

3. The device of claim 1, wherein the float is configured to permit transition of the valve to the open configuration when the level of fluid within the chamber is below a filling threshold.

4. The device of claim 1, wherein the float is configured to occlude the exit flow port when the level of fluid within the chamber is below a draining threshold.

5. The device of claim 4, further comprising an annular ring disposed proximal to the exit flow port, the float being configured to engage the annular ring, such that the engagement between the float and the ring restricts air from exiting the chamber through the exit flow port.

6. The device of claim 1, further comprising a valve seat formed in the chamber proximate the primary flow port.

7. The device of claim 1, wherein the valve guide is configured to guide the valve between the occluding configuration and the open configuration.

8. The device of claim 1, wherein the valve is a disk having a convex surface that is configured to face the primary flow port and a concave surface that is configured to face away from the primary flow port, the disk being configured to be elastically deformed based on the level of fluid within the chamber.

9. The device of claim 1, wherein the secondary flow port comprises a needleless access valve.

10. The device of claim 1, wherein the secondary flow port is connected to the chamber at an angle relative of between about 20 degrees and about 60 degrees from a longitudinal axis of the chamber.

11. The device of claim 1, wherein the float comprises variable interior volume, such that a buoyancy of the float can be adjusted.

12. The device of claim 1, further comprising an indicator that provides visual indication that the float has moved the valve to the occluding configuration.

13. The device of claim 12, wherein the indicator comprises a transparent window in a wall of the chamber, the transparent window forming a lens.

14. The device of claim 1, wherein the chamber comprises an air valve configured to release air from within the chamber.

15. A method of controlling fluid through a Y-site device, comprising:
providing a chamber fluidly coupled between a primary flow port and an exit flow port;
providing a secondary flow port fluidly coupled to the chamber, the secondary flow port configured to conduct fluid to the chamber;
providing a valve guide positioned in the chamber proximate the primary flow port;
providing a valve positioned between the primary flow port and the valve guide;
moving the valve, based on a level of fluid within the chamber, between an occluding configuration and an open configuration, wherein in the occluding configuration, the valve is engaged against the primary flow port to occlude a fluid flow through the primary flow port into the chamber, and in the open configuration, the valve is separated from the primary flow port to permit a fluid flow through the primary flow port into the chamber;
providing a float positioned within the chamber between the valve and the exit flow port; and
moving the float independent of the valve, based on a level of fluid within the chamber such that a portion of the float extends through the valve guide and engages the valve to move the valve to the occluding configuration.

16. The method of claim 15, further comprising, moving the valve to the occluding configuration when the level of fluid within the chamber exceeds a filling threshold.

17. The method of claim 16, further comprising disengaging the float and the valve when the level of fluid is below a filling threshold.

18. The method of claim 15, further comprising the float occluding the exit flow port when the level of fluid within the chamber is below a draining threshold.

19. The device of claim 1, wherein, in the occluding configuration, the float is engaged against the valve, and in the open configuration, the float is separated from the valve.

* * * * *